(12) United States Patent
Loakes et al.

(10) Patent No.: US 7,049,303 B2
(45) Date of Patent: May 23, 2006

(54) INHIBITION OF VIRUSES

(75) Inventors: David Loakes, Cambridge (GB);
Daniel M. Brown, Cambridge (GB);
Kazuo Negishi, Okayama (JP); Kei Moriyama, Okayama (JP); Jan Balzarini, Leuven (BE)

(73) Assignee: Medical Research Council, London (GB)

(*) Notice: Subject to any disclaimer, the term of this patent is extended or adjusted under 35 U.S.C. 154(b) by 183 days.

(21) Appl. No.: 10/207,005

(22) Filed: Jul. 30, 2002

(65) Prior Publication Data

US 2003/0130226 A1   Jul. 10, 2003

(30) Foreign Application Priority Data

Nov. 7, 2001   (GB) .................................. 0126701

(51) Int. Cl.
*A61K 31/70* (2006.01)
(52) U.S. Cl. ............................ 514/45; 514/42; 514/43; 514/46; 514/47; 514/48
(58) Field of Classification Search ................ 514/42, 514/43, 45–48
See application file for complete search history.

(56) References Cited

U.S. PATENT DOCUMENTS 6,063,628 A * 5/2000 Loeb et al. ................. 435/442

FOREIGN PATENT DOCUMENTS

| EP | 0 352 248 | 1/1990 |
|----|-----------|--------|
| WO | WO 90/06319 | 6/1990 |
| WO | WO 96/18398 | 6/1996 |
| WO | WO 96/40164 | 12/1996 |
| WO | WO 98/16184 | 4/1998 |
| WO | WO 98/18324 | 5/1998 |
| WO | WO 99/43691 | 9/1999 |
| WO | WO 01/19360 | 3/2001 |
| WO | WO 01/45691 | 6/2001 |

OTHER PUBLICATIONS

Clercq et al., Antimicrobial Agents and Chemotherapy, 29(3):482-487 (Mar. 1986).
Tiwari et al., Nucleosides, Nucleotides & Nucleic Acids, 20(4-7):743-746 (2001).

* cited by examiner

*Primary Examiner*—Shengjun Wang
(74) *Attorney, Agent, or Firm*—Morgan, Lewis & Bockius, LLP

(57) ABSTRACT

Disclosed is a pharmaceutical composition comprising a ribonucleoside analogue in accordance with general formula I or II as herein defined, in admixture with a physiologically acceptable excipient diluent or carrier.

8 Claims, 4 Drawing Sheets

JA21 (dP)

JA22 (rP)

JA23

JA24

JA25

JA26

JA27

JA28

JA29

JA30

JA31 (rK)

INHIBITION OF VIRUSES

This application claims foreign priority of United Kingdom 0126701.2, filed Nov. 7, 2001.

FIELD OF THE INVENTION

The present invention relates to a method of inducing mutations in viruses, a method of inhibiting the replication of viruses, pharmaceutical compositions for use in inhibiting the replication of viruses, and the use of various compounds in the preparation of medicaments to inhibit viral replication. The invention specifically applies to RNA viruses, that is, viruses which have an RNA genome or which replicate via an essential RNA intermediate.

BACKGROUND OF THE INVENTION

RNA viruses are responsible for many diseases of man and animals. Examples of RNA viruses which are human pathogens include influenza virus, poliovirus, rhinovirus and HIV. A specific example of a pathogenic DNA virus which replicates via an essential RNA intermediate is hepatitis B virus (HBV).

Very few effective antiviral agents are currently available. Certain compounds which are moderately effective against HIV are deoxynucleoside analogues. These act by inhibiting HIV replication by acting as "chain terminators" i.e. causing termination of HIV reverse transcriptase-mediated DNA synthesis. However the efficacy of such drugs is limited because of the emergence of resistant strains of viruses. RNA viruses in general, and HIV in particular, have a very high mutation rate during replication, and this high mutation frequency enhances the likelihood of resistant strains emerging.

Recently the idea has developed that RNA viruses may be close to the "edge of viability". That is, the mutation frequency of such viruses is so high that a comparatively modest increase in mutation frequency may be sufficient to render the great majority of the viral population non-viable, due to the presence of deleterious mutations at essential loci in the viral genome. This well-known concept is known as "error catastrophe" and results with the mutagen ribavirin in the context of poliovirus strongly suggest that the concept is well-founded (Crotty et al, 2000 Nature Medicine 6, 1375–1379; Crotty et al, 2001 Proc. Natl. Acad. Sci. USA 98, 6895–6900).

Loeb et al, (WO 98/18324 and U.S. Pat. No. 6,063,628) disclose the use of ribonucleoside analogues to increase the mutation rate in (and thereby inhibit the replication of) RNA viruses such as HIV or HCV. Loeb et al state that the ribonucleoside analogue may typically be an analogue of cytidine, uridine, adenosine or guanosine, but that analogues of cytidine or uridine (i.e. pyrimidine analogues) are preferred (U.S. Pat. No. 6,063,628; column 3 lines 44–45). Loeb et al do not specifically refer to many purine nucleoside analogues, but adenosine analogues specifically mentioned include: 1,$N^6$-ethenoadenosine, 3-methyladenosine and $N^6$-methyladenosine. Guanosine analogues specifically mentioned include 8-hydroxyguanosine, $O^6$-methylguanosine, $O^6$-ethylguanosine, $O^6$-isopropylguanosine, 3,$N^2$-ethenoguanosine, $O^6$-alkylguanosine, 8-oxo-guanosine, 2,$N^3$-ethenoguanosine, and 8-aminoguanosine.

Interestingly, neither WO 98/18324 nor U.S. Pat. No. 6,063,628 contain any data from experiments performed by the inventors to support the claims made therein. Only one experiment is described in which HIV is passaged in vitro in the presence of either 5-hydroxyuridine or 5-bromocytidine. The results after 4 passages are shown in FIG. 3: no decline in viral titer is apparent in the Figures.

The content of all documents mentioned in this specification is incorporated herein by reference.

SUMMARY OF THE INVENTION

The present invention relates to certain nucleoside analogues which the present inventors, in contrast to the data presented by Loeb et al, have found to be effective in inhibiting RNA virus replication, even within 4 passages in vitro.

In a first aspect the invention provides a method of inhibiting the replication and/or increasing the mutation rate of an RNA virus, the method comprising administering an RNA nucleoside analogue to a cell infected by an RNA virus (as herein defined), the analogue being incorporated by a polymerase into an RNA copy of the viral genomic nucleic acid molecule, wherein the nucleoside analogue conforms to the general formula I or II below:

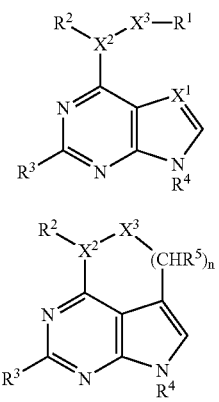

where:
n=1–4, preferably 2–4,
$X^1$=N or CH or $CR^5$
$X^2$=N or S or $CR^5$
$X^3$=$NR^6$ or O or S or $R^6$ when $X^2$=N or $X^3$=$NR^6$ or $R^6$ when $X^2$=S, and $X^3$ is absent when $X^2$=$CR^5$
$R^1$=H or alkyl or aryl or alkaryl or acyl
$R^2$=H or alkyl or aryl or alkaryl or acyl; when $X^2$=S, $R^2$ is absent;
$R^3$=H or $NR^5R^6$ or $NR^5NR^5R^6$ or $NR^5OR^5$
$R^5$=H or alkyl or alkenyl or alkynyl or aryl or alkaryl or acyl
$R^6$=H or alkyl or alkenyl or alkynyl or aryl or alkaryl or acyl and
$R^4$=H or

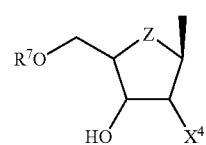

wherein

Z=O or S or CH$_2$ or CHF or CF$_2$ or NR$^5$

X$^4$=OH or F

R$^7$=H or PO$_3^{2-}$ or P$_2$O$_6^{3-}$ or P$_3$O$_9^{4-}$ or a masked phosphate derivative.

Alkyl groups, if present, are preferably methyl groups (desirably unsubstituted). Aryl groups, if present, are preferably phenyl groups, substituted or unsubstituted. Desirably no more than one aryl or alkaryl group is present in a molecule according to the general formulae. Conveniently at least one of R$^1$–R$^6$ is H and preferably at least two of R$^1$–R$^6$ are H.

A masked phosphate derivative is a modified phosphate group in which the negative charge(s) which would normally be present in an unmodified phosphate group are reduced or (more preferably) entirely neutralized by additional moieties. This has the benefit of facilitating transport of compounds comprising the modified phosphate group across a lipid membrane (e.g. across a cell membrane). An example of a masked phosphate derivative is bis-POM/bis-POM PMEA (see Delaney et al, 2001 Antiviral Chemistry and Chemotherapy 12, 1–35) or cycloSal (Meier et al, Eur. J. Org. Chem. 1998, 837).

For present purposes an "RNA virus" is considered to include all viruses with an RNA genome (encompassing both "conventional" RNA viruses and retroviruses) and any virus which requires a genomic RNA intermediate for the purposes of replication. Examples of relevant viruses include ortho- and paramyxoviruses, poliovirus, rhinovirus, retroviruses (especially HIV-1 and HIV-2), hepatitis B and C viruses (HBV and HCV respectively), rotaviruses, flaviviruses and certain arboviruses (e.g. Dengue Fever virus).

The invention encompasses the administration of a ribonucleoside analogue (that is, a base analogue covalently joined to a ribosyl residue) to an infected cell. The administered ribonucleoside analogues may be converted to the corresponding ribonucleotide analogues intracellularly by known enzymes. However it is also possible to perform the invention by administering the base analogue (without an attached ribosyl residue), which base analogue is then converted by phosphoribosylation (in vivo if administered to a living multicellular organism, or intracellularly if administered to a cell in vitro) into a ribonucleotide analogue. Equally the invention encompasses within its scope the administration of a ribonucleotide analogue (that is, a ribonucleoside analogue esterified to a phosphate group, or a di- or tri-phosphate). For the purposes of economy, the compounds of use in the invention are referred to as ribonucleoside analogues, although those skilled in the art will appreciate that the general formulae presented above encompass both base analogues and ribonucleotide analogues, and unless the context dictates otherwise, the term "ribonucleoside" analogue is intended to embrace both base analogue and ribonucleotide analogue. It is generally preferred that the base analogue incorporated in the ribonucleoside analogue is a purine base analogue, which term specifically includes 7-deaza purine analogues.

In some instances it may be preferred to perform the invention by use of base analogues, especially in preference to ribonucleoside analogues, since these may be better absorbed by mammalian subjects following administration in vivo.

Compounds for use in the invention and in accordance with the general formulae presented above are commercially available and/or are readily capable of being synthesised by those skilled in the art using published protocols. Other compounds may be obtained by following the detailed teaching provided in the present specification.

In preferred embodiments Z is O. In the same or other preferred embodiments X$^2$ is N. In the same or other preferred embodiments X$^3$ is O or comprises N. In the same or other preferred embodiments X$^4$ is OH. Desirably, in one embodiment, Z is O, X$^2$ is N, X$^3$ is N or O and X$^4$ is OH. In an especially preferred embodiment Z is O, X$^2$ is N, X$^3$ is O, X$^4$ is OH and R$_1$ is alkyl, especially methyl.

Generally preferred are ribonucleotide analogues which have low toxicity but high viral mutagenicity. Particular examples of preferred ribonucleoside analogues include those illustrated in FIGS. 3, 7 and 11, and the corresponding base analogues and ribonucleotide analogues.

Especially advantageous is the ribonucleoside analogue having the structure shown in FIG. 11, which compound has the full name 2-amino-6-methoxyamino-9-β-D-ribofuranosylpurine, abbreviated for simplicity as rK, and the corresponding base analogue K and ribonucleotide analogue rKP (which expression incorporates in particular mono-, di- and triphosphates). The di- and triphosphates may be referred to as rKDP and rKTP. The inventors have found that rK is active in reducing viral titer, especially the titer of HIV-1 when the virus is grown in vitro in tissue culture.

In order to be effective, the ribonucleoside analogues of the invention need to be incorporated into the RNA copy of the viral genomic nucleic acid with reasonable efficiency and must therefore be recognisable as a suitable substrate by the relevant RNA polymerase inside the host cell. For "conventional" RNA viruses this is an RNA polymerase encoded by the virus. For retroviruses, the relevant RNA polymerase is the RNA polymerase encoded by the host cell. Generally speaking, viral RNA polymerases are less accurate and less discriminating than host cell RNA polymerases and will be more likely to utilise the ribonucleoside analogues.

The inventors have additionally made the surprising discovery that certain ribonucleoside analogues, preferably but not necessarily in accordance with general formulae I or II above, can inhibit retroviral transcription, which finding has not previously been suggested or in any way disclosed in the prior art. Without wishing to be bound by any particular theory, the inventors believe that this is due to an inhibitory effect of the ribonucleoside analogue on transcription promoted by a 5' long terminal repeat ("LTR"), although the mechanism by which this inhibition might be mediated is unknown. Accordingly, preferred ribonucleoside analogues in accordance with the invention are those which exhibit the property of inhibiting retroviral transcription. Methods of assaying compounds for such a property are disclosed herein and may be employed by those skilled in the art to identify ribonucleoside analogues possessing this desirable characteristic. The effect of inhibiting retroviral transcription is that there are fewer RNA copies of the viral genome present in an infected cell: accordingly, at a given concentration of ribonucleoside analogue there are fewer RNA copies of the viral genome which are likely to escape incorporation of the mutagenic ribonucleoside analogue. A preferred compound in this regard is that denoted by the structure shown in FIG. 2 (referred to as rP, for simplicity), and the corresponding base analogue (P) and the corresponding ribonucleotide analogue rPP (especially the triphosphate, rPTP).

It will be appreciated that increasing the mutation rate in the manner of the first aspect of the invention can, in accordance with the concept of error catastrophe, cause a significant increase in the number of non-viable viral particles produced, especially when the ribonucleoside analogue is present at an effective concentration for a plurality of cycles of viral replication, since mutations will accumulate in the viral genome over time. In contrast, although the ribonucleoside analogue will probably be incorporated into messenger RNA in the host cell (resulting in production of mutant polypeptides), mRNA is rapidly turned over and degraded and therefore will not accumulate mutations over time. Equally, the ribonucleoside analogue will generally not be incorporated into the DNA genome of the host cell or, if incorporated, will be removed by the "house-keeping" enzymes which are responsible for maintaining the integrity of the host cell genome. Accordingly, the method of the invention finds therapeutic application in the treatment of RNA virus infections.

Thus, in a second aspect the invention provides a method of treating an RNA virus infection in a human or animal subject, the method comprising administering to a subject infected with an RNA virus, an effective amount of a ribonucleoside analogue in accordance with general formula I or II.

In a third aspect the invention provides a pharmaceutical composition comprising an effective amount of a ribonucleoside analogue in accordance with general formula I or II in admixture with a physiologically acceptable excipient, diluent or carrier.

In a fourth aspect the invention provides a method of making a pharmaceutical composition, the method comprising mixing a ribonucleoside analogue in accordance with general formula I or II with a physiologically acceptable excipient, diluent or carrier. The method optionally includes the further step of packaging the composition in unitary dose form.

In a fifth aspect the invention provides for use of a ribonucleoside analogue according to general formula I or II in the preparation of a medicament to treat an RNA viral infection in a human or animal subject.

The ribonucleoside analogues of use in one or more of the various aspects of the invention will preferably be substantially soluble in water and be readily capable of entering virally-infected cells. Where the compound consists of a base analogue, the compound may generally be ribosylated and phosphorylated in vivo, or at least intracellularly. Where the compound is a ribonucleoside analogue it may typically be phosphorylated to form a ribonucleotide analogue. Possibly it is the ribonucleotide analogue which is integrated into the RNA genome of the RNA virus (or DNA virus which replicates via an essential genomic RNA intermediate), although it is important to note that the inventors make no assumption as to mode of action. Thus the active compound may be the base analogue and/or the ribonucleoside analogue and/or the ribonucleotide analogue. Specifically in respect of integrating retroviruses, such as HIV, the presence of the active compound probably leads to mutation by the viral reverse transcriptase during DNA synthesis prior to integration into the host genome, which mutations are not recognisable by repair enzymes; over several cycles such mutations will accumulate.

Pharmaceutical compositions in accordance with the invention may be administered by any conventional route known to those skilled in the art. The preferred route is oral administration, but the composition may alternatively be administered, for example, intravenously, subcutaneously, transdermally, or via a rectal or intranasal route.

The composition may be administered as a solid (e.g. in the form of a tablet, pill, capsule, powder or the like) or may be a liquid (e.g. solution, suspension), semi-solid (e.g. a gel), aerosol or spray.

Physiologically acceptable excipients, diluents and carriers are well known to those skilled in the art of medical formulations and include, for example: saline, Ringer's solution, distilled water, dextrose solution, calcium carbonate, silicates, starches and modified starches and plant-derived polysaccharide gums and gels (e.g. xanthan gum; carrageenans and the like).

An "effective amount" of a ribonucleoside analogue or pharmaceutical composition comprising the same is understood to mean, for present purposes, an amount sufficient to cause a measurable decrease in the viral titer in suitable samples (e.g. blood, saliva, or tissue biopsy specimens) taken from the subject, or a measurable decrease in the amount of viral antigen detected in such samples, or a discernible amelioration in the symptoms of the viral infection experienced by the subject. Methods of obtaining suitable samples from a subject, and of analysing same to measure viral titer or viral antigen (e.g. by ELISA or other immunoassay) are well known to those skilled in the art.

The appropriate dose of the ribonucleoside analogue will depend on several factors, such as the body mass of the subject, level of toxicity (if any) of the analogue, the age of the subject and the severity of the viral infection (and/or any additional condition afflicting the subject). Guidance is given in U.S. Pat. No. 6,063,628. Conveniently the dose of ribonucleoside analogue will be in the range 1 mg/Kg body weight to 500 mg/Kg per day, preferably in the range 5 mg/Kg–250 mg/Kg, more preferably 10 mg–100 mg/Kg.

Typically a dose at the lower end of the acceptable range is administered to the subject and, if there is no discernible improvement in the subject's condition, the dose may be increased if there are no contra-indications, until an effective dose is achieved. By such trial and error clinicians will readily be able to find an appropriate dose for any particular subject.

Advantageously the pharmaceutical composition in accordance with the invention may comprise more than one anti-viral agent. For instance, the composition may comprise a plurality of different ribonucleoside analogues, each being in accordance with general formula I or II defined above.

Additionally, or alternatively, the composition may comprise one or more antiviral agents which do not conform to general formula I or II. Examples include conventional antiviral agents such as ribavirin, AZT, HIV protease inhibitors, and compounds of the sort explicitly disclosed in U.S. Pat. No. 6,063,628. The other aspects of the invention may conveniently reflect such embodiments.

Alternatively, the method of treating the subject may comprise separate administration of a further pharmaceutical composition comprising an additional anti-viral agent, such as those aforementioned, or a substance that reduces the intra-cellular concentration of the naturally-occurring ribonucleotide(s) with which the ribonucleoside analogue must compete for incorporation into the viral RNA genome.

BRIEF DESCRIPTION OF THE DRAWINGS

The invention will now be further described by way of illustrative example and with reference to the accompanying drawings, in which.

EXAMPLES

Example 1

Synthesis of Purine Ribonucleoside Analogues

Figure 1:
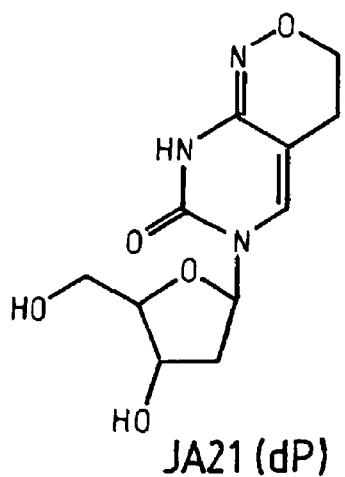
FIG. 1 shows the structural formula of a deoxyribonucleoside analogue, dP.
Figure 2:
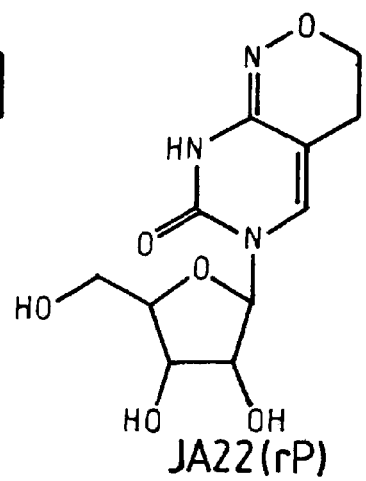
FIG. 2 shows the structural formula of a ribonucleoside analogue rP, the 'ribo' equivalent of the compound shown in FIG. 1.
Figure 3:
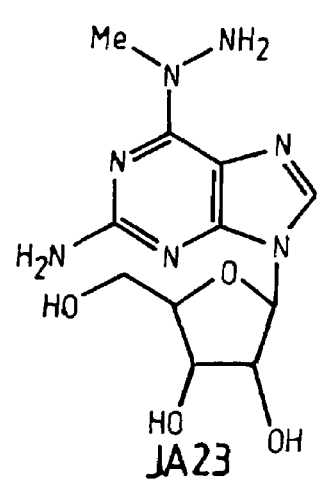
FIGS. 3–11 show the structural formula of various ribonucleoside analogues in accordance with general formula I or II identified above.
Figure 4:
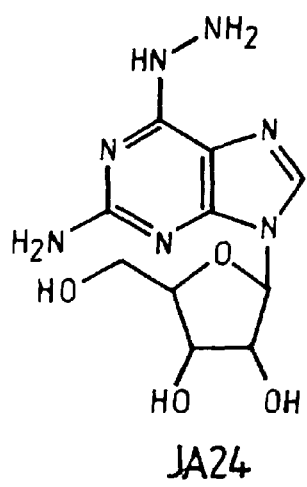
Figure 5:
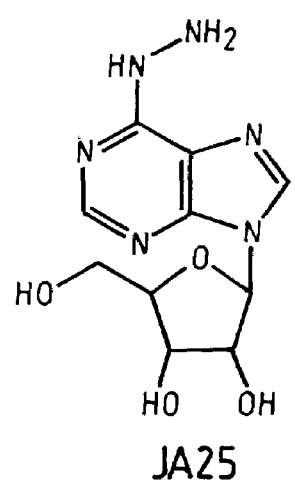
Figure 6:
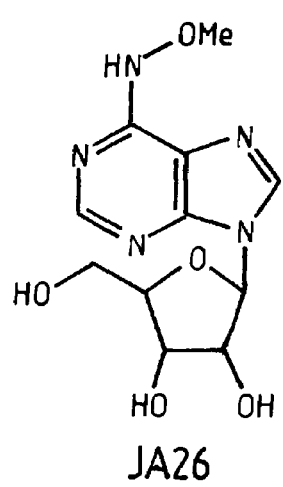
Figure 7:
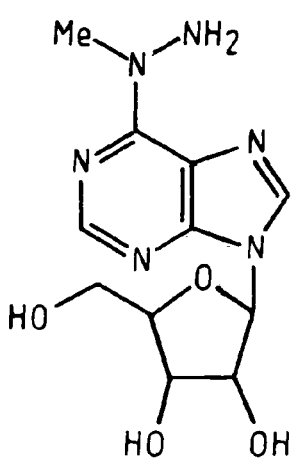
Figure 8:
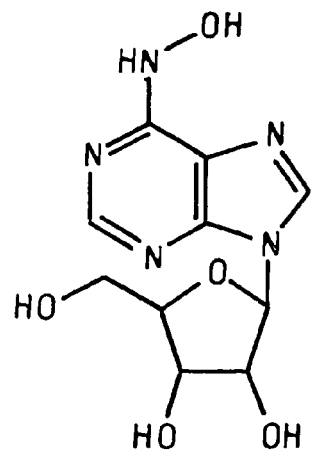
Figure 9:
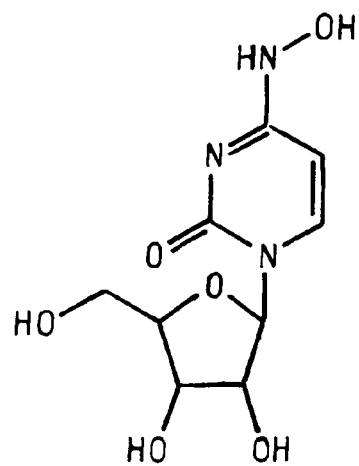
Figure 10:
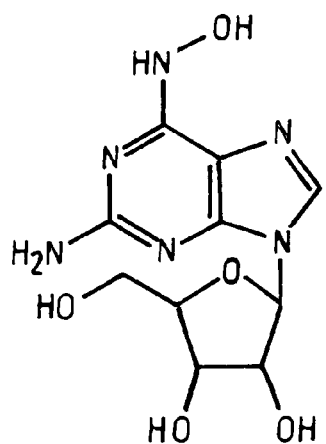
Figure 11:
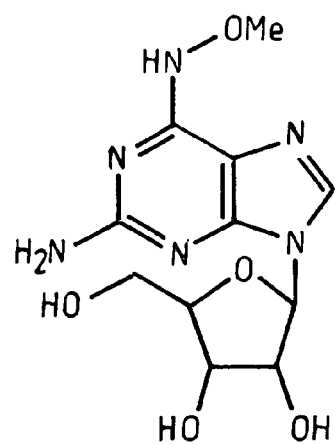

The inventors synthesised several ribonucleoside analogues in accordance with general formula I or II, and also a ribonucleoside ($N^4$-hydroxycytidine) specifically mentioned by Loeb et al in U.S. Pat. No. 6,063,628. For brevity the synthesised compounds are referred to herein as JA22–JA31. An additional compound, JA21, was synthesised and used as a control. JA21 is the deoxyribonucleoside equivalent of the ribonucleoside analogue JA22. JA29 is the compound indicated by Loeb et al as being useful in increasing the mutation frequency of RNA viruses (although no data are presented by Loeb et al in support of that assertion). The table below (Table 1) indicates the systematic name of each of the compounds referred to as JA21–JA31, and also any trivial name if such a name has been used previously.

TABLE 1

| Compound Number | Systematic Name | Trivial Name (if any) |
|---|---|---|
| JA21 | 6-(2-deoxy-β-D-ribofuranosyl)-3,4-dihydro-8H-pyrimido[4,5-c][1,2] oxazin-7-one | dP |
| JA22 | 6-(β-D-ribofuranosyl)-3,4-dihydro-8H-pyrimido[4,5-c][1,2] oxazin-7-one | rP |
| JA23 | 2-amino-$N^6$-methyladenosine | — |
| JA24 | $N^6$-amino-9-β-D-ribofuranosyl-2,6-diaminopurine | — |
| JA25 | $N^6$-aminoadenosine | — |
| JA26 | $N^6$-methoxyadenosine | — |
| JA27 | $N^6$-amino-$N^6$-methyladenosine | — |
| JA28 | $N^6$hydroxyadenosine | — |
| JA29 | $N^4$-hydroxycytidine | — |
| JA30 | 2-amino-$N^6$-hydroxyadenosine | — |
| JA31 | 2-amino-6-methoxyamino-9-β-D-ribofuranosylpurine | rK |

The structures of compounds JA21–JA31 are shown in FIGS. 1–11 respectively.

As examples of compounds of use in accordance with the present invention and in accordance with general formula I or II, JA23–JA31 (except JA29) were synthesised from 6-chloro-9-β-D-ribofuranosylpurine or 2-amino-6-chloro-9-β-D-ribofuranosylpurine (Aldrich). These were treated with the following available reagents: hydroxylamine hydrochloride, methoxyamine hydrochloride, N,O-dimethyl hydroxylamine hydrochloride, anhydrous hydrazine and N-methylhydrazine.

Example of General Method

2-Amino-6-methoxyamino-9-β-D-ribofuranosylpurine-(JA31)

Synthesis of this compound has been described previously (Ueda, et al. Chem. Pharm. Bull., 1978, 26, 2122).

The 2-amino-6-chloropurine derivative (302 mg; 1 mMol), methoxyamine hydrochloride (160 mg; 4 equiv.) and triethylamine (0.2 ml) in ethanol (9 ml) were heated overnight at 85° C. in a sealed bottle shielded from light. Complete reaction was judged by thin layer chromatography (tlc.) in 20% MeOH—$CH_2Cl_2$. Evaporation in vacuo then trituration with ethanol of the residue gave the product as a white powder (90%) which gave needles on crystallisation from dioxan-water.

In the synthesis of compounds from 6-chloro-9-β-D-ribofuranosylpurine the reaction conditions required lower temperatures and shorter reaction times.

The synthesis of compounds in accordance with general formula I or II has been described in a number of other publications:

JA23, 24, 27 and 30, see Taito et al, (1964 Chem. Pharm. Bull. 12, 951);
JA25, see Johnson et al, (1958 J. Amer. Chem. Soc. 80, 699);
JA26, see Fuji et al, 1991 Chem. Pharm. Bull. 39, 39);
JA28, see Giner-Sorolla et al, (1966 J. Med. Chem. 9, 143).

All of the compounds synthesised were recrystallized, characterised by nmr and shown to be substantially pure.

Example 2

Following synthesis, the various compounds were tested in vitro for toxicity, by measuring the $IC_{50}$ (i.e. the concentration which caused 50% inhibition) in respect of the inhibitory effects of the compounds on the proliferation of human T-lymphocytes (CEM/O cells). The results are shown below in Table 2.

TABLE 2

| Compound | $IC_{50}$[a] (µM) |
|---|---|
| JA21 | 690 ± 14 |
| JA22 | 698 ± 11 |
| JA23 | 622 ± 8 |
| JA24 | 62 ± 6 |
| JA25 | 12 ± 3 |
| JA26 | 44 ± 2 |
| JA27 | 17 ± 2 |
| JA28 | 156 ± 15 |
| JA29 | 16 ± 1 |
| JA30 | 78 ± 3 |
| JA31 | 377 ± 62 |

[a]50% inhibitory concentration.

Example 3

Having established an indication of the toxicity of the various compounds, the ribonucleoside analogues were then tested to determine whether they exhibited any effect on the replication of RNA viruses in in vitro cell cultures.

HIV-1 infected CEM cells were subcultured every 4–5 days in the presence of sub-toxic concentrations (in the range of 10–20% of their respective $IC_{50}$ value) of the compounds under test. At each sub-culture, cell-free supernatant (10–20 µl) was transferred to fresh 1 ml cell cultures. At regular intervals the cultures were inspected microscopically to assess the extent of any cytopathic effect (giant cell formation). As an alternative, it is also possible to perform an immunoassay to quantify viral p24 production.

The preliminary results for up to 7 passages are shown below in Table 3.

TABLE 3

| Drug | Concentra- tion (µM) | Passage number[a,b] | | | | | | |
|---|---|---|---|---|---|---|---|---|
| | | 1 | 2 | 3 | 4 | 5 | 6 | 7 |
| JA-21 (dP) | 400 | 100 | 100 | 25 | 50 | 37 | 12 | 6 |
| JA-22 (rP) | 400 | 100 | 100 | 100 | 100 | 100 | 100 | 100 |
| JA-23 | 400 | 100 | 100 | 12 | 25 | 3 | 0 | 0 |
| JA-24 | 10 | 100 | 100 | 25 | 100 | 100 | 100 | 25 |
| | 4 | 100 | 100 | 19 | 100 | 100 | 100 | 12 |
| JA-25 | 2 | 100 | 100 | 100 | 100 | 100 | 100 | 100 |
| | 0.8 | 100 | 100 | 87 | 100 | 100 | 100 | 100 |
| JA-26 | 10 | 100 | 100 | 25 | 100 | 100 | 12 | 3 |
| | 4 | 100 | 100 | 25 | 100 | 100 | 12 | 3 |
| JA-27 | 4 | 100 | 100 | 6 | 25 | 25 | 0 | 0 |
| JA-28 | 40 | 100 | 100 | 50 | 100 | 100 | 75 | 6 |
| | 20 | 100 | 100 | 19 | 100 | 100 | 100 | 100 |
| JA-29 | 2 | 100 | 100 | 25 | 100 | 100 | 100 | 100 |
| | 0.8 | 100 | 100 | 12 | 100 | 100 | 100 | 100 |
| JA-30 | 10 | 100 | 100 | 25 | 100 | 100 | 100 | 50 |
| JA-31 (rK) | 50 | 100 | 100 | 0 | 0 | 0 | 0 | 0 |
| | 20 | 100 | 100 | 3 | 19 | 12 | 0 | 0 |
| Control (no drug) | — | 100 | 100 | 25 | 100 | 100 | 100 | 100 |

[a]Subcultivation of the drug-treated HIV-1(III$_B$) exposed CEM cell cultures was performed every 5 days.
[b]Data represent the percentage of cytopathic effect (giant cell formation) as recorded microscopically.

The results show that JA31 (rK) in particular is effective at inhibiting the replication of RNA viruses as exemplified by HIV. Other compounds also appear to be moderately effective: JA23 and JA27 in particular. JA29, mentioned by Loeb et al, does not demonstrate any antiviral activity in this assay.

In order to demonstrate that the reduction in viral titer, as evidenced by the decline in observed cytopathic effect, is due to induction of accumulated mutations in the viral genome, proviral DNA will be isolated from the cultures and the sequence of the reverse transcriptase gene determined by routine DNA sequencing reactions. The determined sequence can be compared with the known sequence of the original input virus and the number of mutations calculated relative to those in the virus in the control culture.

Further Studies

Mechanism of action studies will be undertaken to study the effect of the 5'-triphosphate derivatives of the ribonucleotide analogues on human and viral RNA polymerase-catalysed RNA synthesis and HIV-1 reverse transcriptase-catalysed conversion of nucleotide analogue-containing RNA to DNA. Also, the substrate affinity of recombinantly produced ribonucleoside kinases for the ribonucleoside analogues and their efficacy of conversion of the ribonucleoside analogues to their 5'-monophosphates will be determined. Insights in the above-mentioned characteristics of the ribonucleos(t)ide analogues should allow optimisation of the viral mutagenicity of the compounds whilst ideally minimising toxicity, so as to enhance the therapeutic usefulness of the compounds. Masked phosphate derivatives of the ribonucleoside analogues will also be investigated.

Example 4

Other experiments were performed using ribonucleoside analogues present as the phosphorylated ribonucleotide. For example, the triphosphate of rK, referred to as rKTP, was synthesised as described by Moriyama et al, (1998 Nucl. Acids Res. 26, 2105). The triphosphate of rP, rPTP, was prepared in an analogous manner.

These two compounds were then investigated for an inhibitory effect on the replication of HIV in persistently infected Molt4/IIIB cells, or acutely infected MT4/IIIB cells. The compounds were compared with equivalent concentrations of dideoxycytidine (ddC) or dideoxycytosine triphosphate (ddCTP), or a negative control (no drug).

Effect on Persistently-infected Cells 2 nmol of the relevant drug (final concentration 1 µM) was mixed with 4 µl of liposome DMRIE-C (Gibco BRL) in 800 l of serum-free RPMI 1640 medium (Sigma). After incubating for 45 minutes at room temperature, $10^5$ Molt4/IIIB cells in 200 l of serum-free RPMI 1640 medium were added and held at 37° C. for 4 hours. At the end of this interval 1 ml of RPMI 1640 medium supplemented with 20% serum was added and the mixture cultured at 37° C. at 24 hrs, 72 hrs and 5 days, aliquots of supernatant were collected and the amount of p24 antigen present was quantified using the Lumipuls™ system (Fuji Rebio). The results are shown in FIG. 12.

Effect on Acutely-infected Cells $10^3$ pfu of HIV$_{IIIB}$ were added to $10^5$ MT4 cells in 1 ml of serum-free RPMI 1640 medium and incubated for 90 minutes at 37°. The cells were washed three times in serum-free medium and resuspended in 200 µl of serum-free medium. Drug administration (100 nM final concentration), culture and p24 assay were then performed as above. The results are shown in FIG. 13.

Figure 12:
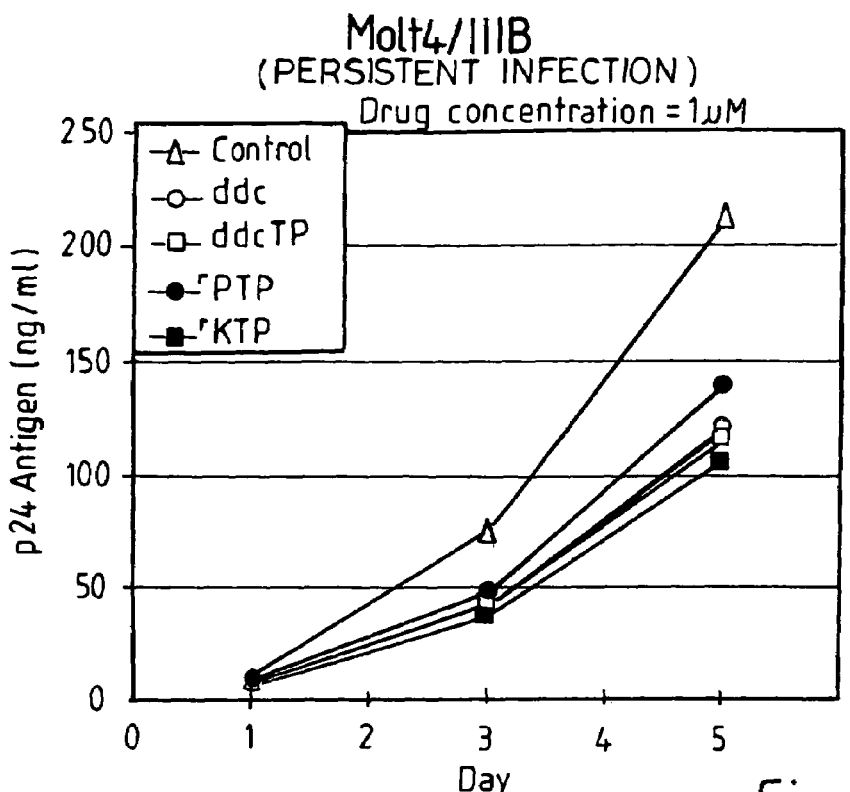
FIGS. 12 and 13 are graphs of p24 antigen (ng/ml) against time (in days)

FIG. 12 is a graph of viral titer (as measured by amount of p24 antigen in ng/ml) against time (in days), showing the results for cultures of persistently-infected Molt4/IIIB cells with no drug ("Control", triangles), or 1M final concentration of ddC (open circles), ddCTP (open squares), PTP (filled circles) or rKTP (filled squares). FIG. 13 is a graph of p24 antigen (in ng/ml) against time (in days) for cultures of acutely-infected MT4/IIIB cells in the presence of drugs at a final concentration of 100 nM, the legend is as for FIG. 12.

Figure 13:
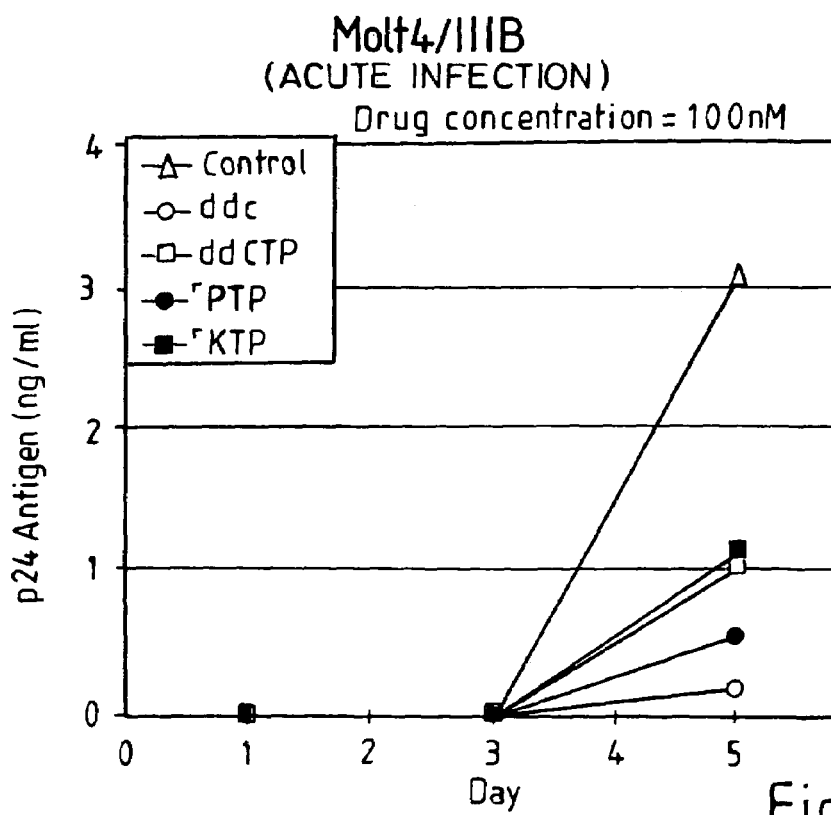

The results illustrated in FIGS. 12 and 13 show that both rKTP and rPTP significantly inhibit viral replication compared to controls, and reduce viral titers to levels comparable with known dideoxy chain-terminating compounds which inhibit reverse transcriptase. The ribonucleotide analogues of the invention are believed, however, to be less vulnerable to the evolution of resistant virus strains.

Example 5

Mutations Induced on HIV-1 pol Gene of MT4/IIIB by PTP or KTP

Genomic DNA of MT4/IIIB was collected 3 days after drug administration (final concentration was 100 nM) by DNeasy Tissue Kit (QIAGEN). A part of the pol gene (873 bp) was amplified by 2-step polymerase chain reaction (2-step PCR). 1 st PCR reaction mixture contained 50 pmol of forward primer-1 (5'-GGTACAGTATTAGTAGGACC-3'), 50 pmol of reverse primer-1 (5'-TGTGTCAGT-TAGGGTGACAA-3'), 200 µM each dNTP, 5 µl of collected genomic DNA, 3 U of Pfu DNA polymerase (Promega), 20 mM Tris-HCl pH 8.8 10 mM KCl, 10 mM $(NH_4)_2SO_4$, 2 mM $MgSO_4$, 0.1% Triton X-100, and 0.1 µg/µl BSA in 50 µl and was divided into five tubes. Each mixture was incubated for 2 min at 95° C. Then it was applied to a thermal cycle reaction comprising 95° C., 1 min; 52° C., 30 sec; and 72° C., 2 min for 45 cycles, followed by incubation for 5 min at 72° C., the cycling controlled by Mastercycler gradient apparatus (Eppendorf).

The 2nd PCR reaction mixture contained 50 pmol of forward primer-2 (5'CAGGGATTAGATATCAGTAC-3'), 50 pmol of reverse primer-2 (5'-TCTCTAACTGGTACCAT-AAT-3'), 200 µM each dNTP, 1 µl of 1st PCR product from each tube, 1.5 U of Pfu DNA polymerase (Promega), 20 mM Tris-HCl pH 8.8, 10 mM KCl, 10 mM $(NH_4)_2SO_4$, 2 mM $MgSO_4$, 0.1% Triton X-100, and 0.1 g/1 BSA in 50 µl and was similarly divided into five tubes. Each mixture was incubated for 2 min at 95° C. Then it was applied to a thermal cycle reaction comprising 95° C., 1 min; 52° C.; 30 sec; and 72° C., 2 min. for 30 cycles, followed by incubation for 5 min at 72° C.

Divided 2nd PCR products (total twenty-five tubes for one sample) were collected into one tube, ethanol precipitated, and digested by EcoRV and KpnI. After ligation with pBluescriptIISK(+), the constructed plasmid was introduced into Escherichia coli DH5 by electroporation. Cloned PCR product was then applied to standard DNA sequencing reaction using forward sequencing primer (5'-AAAGCTG-GAGCTCCACCGCG-3') or reverse sequencing primer (5'-AGTGAGCGCGCGTAATACGACTCACTA-TAGGGC-GAATTGG-3') and the Thermo Sequenase II dye terminator cycle sequencing kit (Amersham Pharmacia Biotech). Electrophoresis and analysis was carried out by DNA sequencer 378A (Applied Biosystems).

The sequencing revealed that the presence of either rPTP or rKTP increased the mutation frequency, according to the results presented in Table 4 below.

TABLE 4

| | Transition G-to-A | Transversion T-to-A | Total | Sequenced (nucleotides) | Frequency $(\times 10^{-3})$ |
|---|---|---|---|---|---|
| Control | 1 | 2 | 3 | 3,113 | 0.96 |
| PTP | 3 | 6 | 9 | 4,809 | 1.9 |
| KTP | — | 6 | 6 | 4,642 | 1.3 |

Example 6

Figure 14:
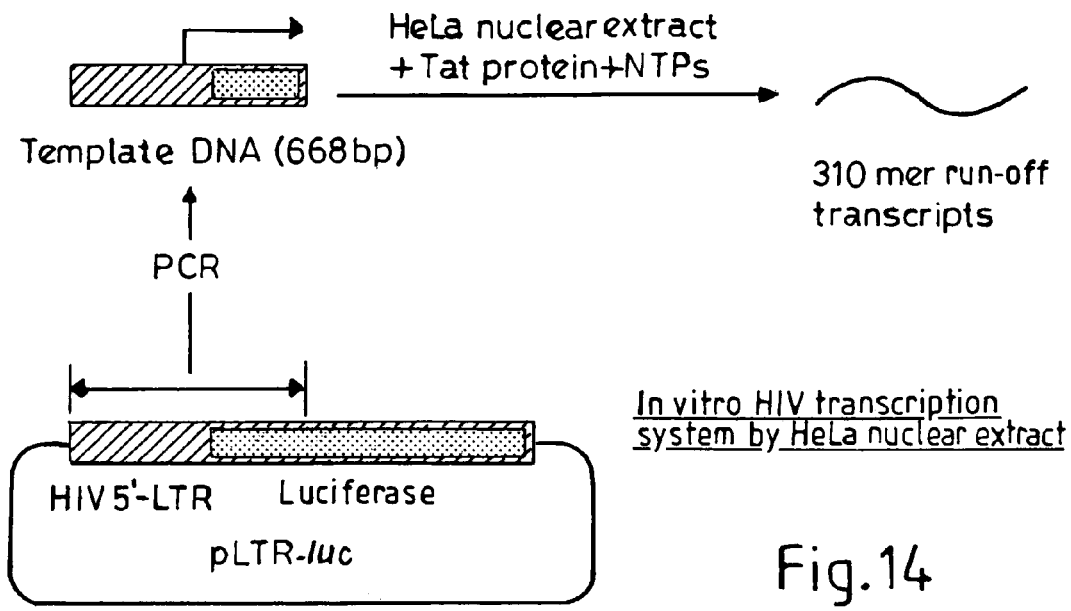
FIG. 14 is a schematic representation of a transcription system of use in screening ribonucleoside analogues for use in the present invention.

The inventors constructed an in vitro transcription system promoted by HIV 5'-long terminal repeat (LTR) using HeLa nuclear extract supplemented with HIV Tat protein. A 668 bp PCR product from pLTR-luc plasmid, which includes HIV 5'-LTR promoter and luciferase gene, was used as a DNA template for a transcription reaction. From this template, 310-mer run-off transcripts were produced. The system is illustrated schematically in FIG. 14.

Figure 15:
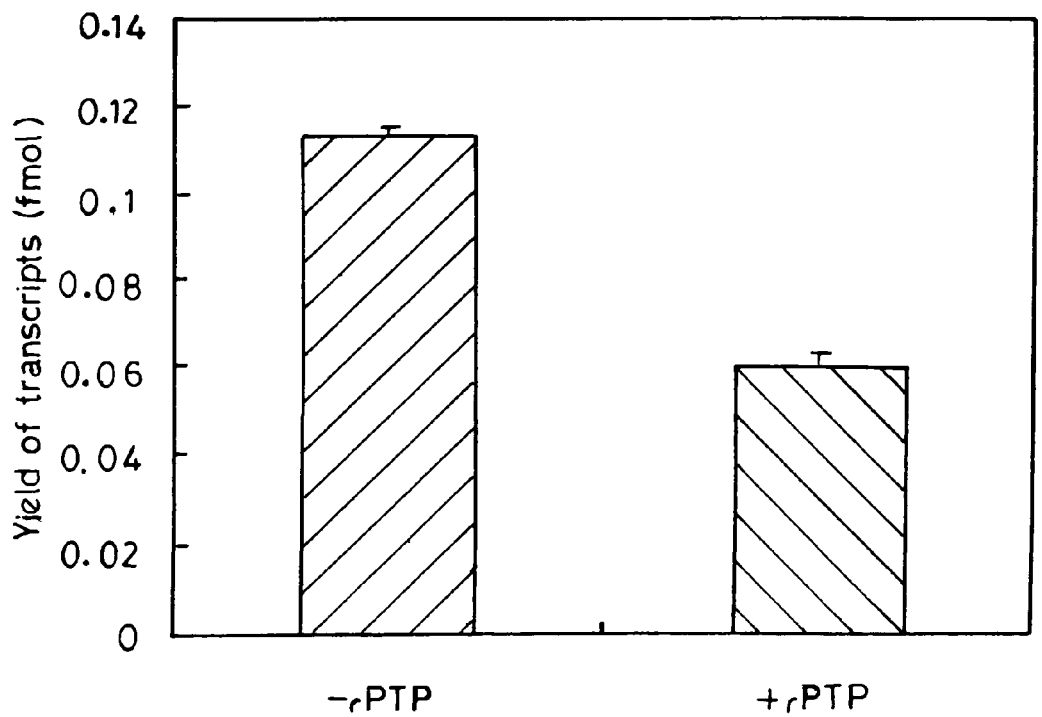
FIG. 15 is a bar chart showing the amount of RNA transcript produced (in femtomoles) by a transcription system of the sort illustrated in FIG. 14, in the presence or absence of a ribonucleotide analogue rPTP.

The effect of incorporation of rPTP, at 200M, in transcription reactions was investigated. The reaction mixture contained conventional nucleotide triphosphates (ATP, GTP, CTP and UTP) at 50 M (the GTP being $^{32}P$ radio labelled with 10 Ci of radioactivity), +/− 200 M PTP, 100 ng of template DNA, 40 Units of RNase inhibitor (Wako), 1 l of diluted (1:20) Tat protein and 8 units of HeLa cell nuclear extract in 1×transcription buffer (10 mM HEPES pH 7.9, 2 mM DTT, 6.25 M $ZnSO_4$, 100 mM KCl, 20% glycerol, 4 mM $MgCl_2$). The reaction mixture was incubated for 10 minutes at 30° C. and the reaction terminated by adding 7 volumes of stop solution (300 mM Tris. HCl pH 7.4, 300 mM sodium acetate, 0.5% SDS, 2 mM EDTA, 3 g/ml tRNA). Transcripts were then purified by phenol/chloroform extraction and ethanol precipitation. Whole samples were loaded on a 5% polyacrylamide gel and subjected to electrophoresis (40W, for 2 hours). The intensity of the bands corresponding to the 310 mer transcripts was measured by a BAS-2000 image analyser (Fujifilm). The intensity of the band in the control reaction (no PTP) was considered to be 100%. The results of the control reaction and the rPTP reaction are shown in FIG. 15 below. This shows that the presence of rPTP at 200 M reduced the amount of transcript produced by nearly 50%.

Example 7

The foregoing examples are primarily concerned with demonstrating an inhibitory effect of various ribonucleoside analogues on the replication of HIV. However, as explained above, the compositions of the present invention should also find use in combatting infections caused by "conventional" RNA viruses.

In general terms, those skilled in the art can readily ascertain the likely efficacy of various ribonucleoside analogues, by incubating an RNA virus of interest with suitable susceptible host cells in the presence or absence of various concentrations of the ribonucleoside analogue(s) under test, and using an appropriate parameter to measure the amount of viral replication. Suitable parameters might include, for example, an assay of numbers of pfu of virus after a certain length of incubation, or an assay of viral antigen, or amount of cytopathic effect.

A specific example of a suitable screening assay, to identify compounds effective in inhibiting replication of poliovirus, is set forth below. Essentially similar protocols, suitably modified, could be employed to screen for compounds active against other "conventional" RNA viruses.

HeLa cells are propagated in D-MEM/F-12 media (Invitrogen) supplemented with dialyzed fetal bovine serum (2%, Invitrogen). For poliovirus infection assays, cells are plated in 24-well dishes ($1\times10^5$ cells/well) 48 h before the experiment, test compounds are preloaded 24 hours before the experiment, and cells are infected with 2000 pfu poliovirus per well. Upon reaching 100% cytopathic effect (CPE), virus is harvested by freeze-thaw and serial dilutions are plaqued on 6-well dishes of confluent HeLa S3 cells. After 72 hours, cells are stained with Crystal Violet (0.2% in 20% ethanol) to visualize plaques. Time to 100% CPE is recorded as the number of days required for poliovirus (2000 pfu) to cause visibly complete cell death.

The invention claimed is:
1. A method of treating an RNA virus infection in a human or animal subject, the method comprising the step of administering to a subject infected with an RNA virus an effective amount of a ribonucleoside analogue of the formula I:

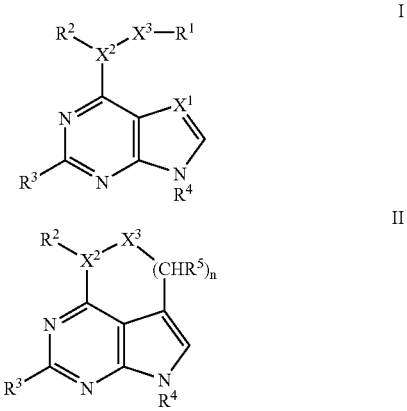

where:
$X^1$=N or CH or $CR^5$
$X^2$=N

X³=NH₂ or O
R¹=H or alkyl or aryl or alkaryl or acyl
R²=H or alkyl or aryl or alkaryl or acyl;
R³=H or NR⁵R⁶ or NR⁵NR⁵R⁶ or NR⁵OR⁵
R⁵=H or alkyl or alkenyl or alkynyl or aryl or alkaryl or acyl
R⁶=H or alkyl or alkenyl or alkynyl or aryl or alkaryl or acyl and
R⁴=

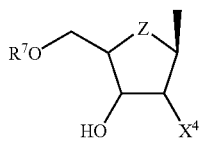

wherein
Z=O
X⁴=OH
R⁷=H or PO₃²⁻ or P₂O₆³⁻ or P₃O₉⁴⁻ or a masked phosphate derivative.

2. A method according to claim 1, comprising administering to the subject an effective amount of said analogue in admixture with a physiologically acceptable excipient, diluent or carrier.

3. he method which comprises administering a ribonucleoside analogue according to claim 1 to treat an RNA virus infection in a human or animal subject by inhibiting LTR-mediated transcription of viral nucleic acid.

4. The method of claim 1 where said analogue, after administration, gives rise to a chemical entity which, inside a cell of the subject, is incorporated into a RNA molecule by RNA polymerase present in the cell.

5. The method of claim 1 wherein R¹ is alkyl.

6. The method of claim 1 wherein the analogue is 2-amino-6-methoxyamino-9-β-D-ribofuranosylpurine.

7. The method of claim 1 wherein said analogue is administered with a further antiviral agent.

8. The method of claim 7 wherein the further antiviral agents is an inhibitor of reverse transcriptase.

* * * * *

UNITED STATES PATENT AND TRADEMARK OFFICE
CERTIFICATE OF CORRECTION

PATENT NO. : 7,049,303 B2  
APPLICATION NO. : 10/207005  
DATED : May 23, 2006  
INVENTOR(S) : Loakes et al.

It is certified that error appears in the above-identified patent and that said Letters Patent is hereby corrected as shown below:

Col. 12, line 55, delete "II".

Col. 12, lines 55 to 63, delete the following formula:

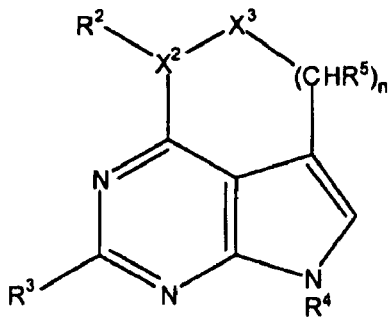

Signed and Sealed this

Twenty-ninth Day of April, 2008

JON W. DUDAS  
*Director of the United States Patent and Trademark Office*